United States Patent [19]

Wright et al.

[11] 3,980,660

[45] Sept. 14, 1976

[54] N,N''(PYRIDINEDIYL)DIOXAMATE COMPOUNDS

[75] Inventors: John B. Wright; Charles M. Hall; Anthony A. Sinkula, all of Kalamazoo, Mich.

[73] Assignee: The Upjohn Company, Kalamazoo, Mich.

[22] Filed: June 10, 1974

[21] Appl. No.: 477,814

[52] U.S. Cl. .......................... 260/295 PA; 424/245; 424/248; 424/250; 424/263; 424/266; 260/247.2 A; 260/268 H; 260/270 E; 260/293.69; 260/294.8 R; 260/294.9; 260/295.5 A

[51] Int. Cl.² ................................ C07D 213/75

[58] Field of Search . 260/295 R, 295 AM, 295.5 A, 260/295 PA, 247.2 A, 270 E, 293.69, 294.8 R, 268 H

[56] References Cited
UNITED STATES PATENTS 3,639,249   2/1972   Luethi et al. ................... 260/397.6

*Primary Examiner*—Natalie Trousof
*Assistant Examiner*—R. W. Ramsuer
*Attorney, Agent, or Firm*—Martin B. Barancik; Roman Saliwanchik

[57] ABSTRACT

It has now been discovered, that compounds of FIG. 1

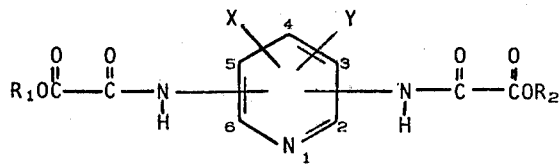

are useful in the prophylactic treatment of sensitized humans and animals for allergy and all anaphylactic reactions of a reagin or non-reagin mediated nature. Additionally, the compounds are intermediates to the biologically active dioxamic acids and their salts. The compounds are formulated with pharmaceutical carriers for oral, parenteral, inhalation or rectal means of administration.

15 Claims, No Drawings

N,N''(PYRIDINEDIYL)DIOXAMATE COMPOUNDS

BRIEF SUMMARY OF THE INVENTION

It has now been discovered that novel compounds of FIG. 1 are useful in the prophylactic treatment of sensitized humans and animals for allergy and all anaphylactic reactions of a reagin or non-reagin mediated nature. Additionally, the compounds are intermediates to the biologically active dioxamic acids and their salts. The compounds are formulated with pharmaceutical carriers for oral, parenteral, inhalation or rectal means of administration.

DETAILED DESCRIPTION OF THE INVENTION

In accordance with this invention, there are provided compounds represented by FIG. 1, and hereafter referred to as Group A,

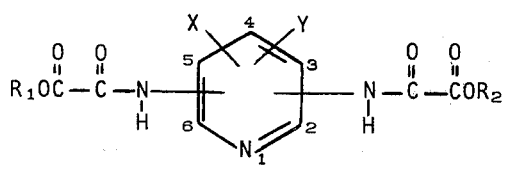

(1)

and N-oxides thereof wherein each

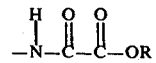

group is located anywhere on the carbon ring with the proviso that one group cannot be ortho to the other group;

X and Y can be the same or different and are selected from the group consisting of hydrogen, alkyl from one through four carbon atoms, phenyl, alkoxy from one through four carbon atoms, nitro, amino, trifluoromethyl, halogen, cyano and

wherein D is selected from the group consisting of hydrogen, alkyl from 1 through 6 carbon atoms and a physiologically acceptable metal or amine cation.

$R_1$ and $R_2$ are the same or different and are selected from the group consisting of hydrogen; a physiologically acceptable metal or amine cation; alkyl of 7 to 12 carbon atoms, inclusive; cycloalkyl of four to eight carbon atoms, inclusive;

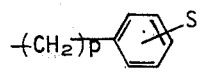

wherein $p$ is an integer of zero to four, inclusive, and S is selected from the group consisting of hydrogen, alkyl of one to six carbon atoms, inclusive, phenyl, halogen, trigluoromethyl, hydroxy, alkoxy of 1 to 4 carbon atoms, inclusive, amino, nitro, carboxy, cyano, and

wherein $R_3$ and $R_4$ are the same or different and are selected from the group consisting of hydrogen and alkyl of one to four carbon atoms, inclusive; with the proviso that when $p$ is zero, S is not hydrogen; and

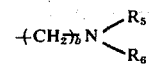

wherein $b$ is an integer of 2 to 4, inclusive, and $R_5$ and $R_6$ are the same or different and are selected from the group consisting of hydrogen and alkyl of 1 to 4 carbon atoms, inclusive, and when $R_5$ and $R_6$ are taken together with the nitrogen atom to which they are attached form a saturated heterocyclic of 3 to 6 ring carbon atoms, inclusive; with the further proviso that when one of $R_1$ and $R_2$ is hydrogen or a physiologically acceptable metal or amine cation, the other variable is not hydrogen or a physiologically acceptable metal or amine cation; and physiologically acceptable acid addition salts thereof.

Another group of compounds, hereafter referred to as Group B, are compounds where X and Y are the same or different and are selected from the group consisting of hydrogen, alkyl of one to four carbon atoms, inclusive, phenyl, alkoxy of one to four carbon atoms, inclusive, nitro, trifluoromethyl, halogen, cyano and

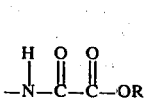

the location of the

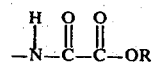

groups and $R_1$ and $R_2$ are identified as in Group A.

A further group of compounds, hereafter referred to as Group C, are compounds wherein the

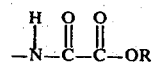

groups are located at the 2 and 6 positions or the 3 and 5 positions. X and Y and $R_1$ and $R_2$ are defined as in Group B.

A still further group of compounds, hereafter referred to as Group D, are compounds wherein the location of the

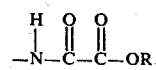

groups are defined as in Group C, X is hydrogen, Y is selected from the group consisting of hydrogen, alkyl of one to four carbon atoms, inclusive, alkoxy of 1 to 4 carbon atoms, inclusive, nitro, trifluoromethyl, halogen, cyano, and

$R_1$ and $R_2$ are the same or different and are selected from the group consisting of alkyl of seven to ten carbon atoms, inclusive; cycloalkyl of four to seven carbon atoms, inclusive; and

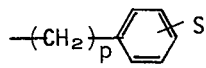

wherein $p$ is an integer of 0 to 4, inclusive, and S is selected from the group consisting of hydrogen, alkyl of 1 to 4 carbon atoms, inclusive, alkoxy of 1 to 4 carbon atoms, inclusive, halogen, carboxy, and cyano, with the proviso that when $p$ is zero, S is not hydrogen.

A further group of compounds, hereafter referred to as Group E, are compounds wherein X, $R_1$, $R_2$ and the location of the

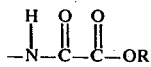

groups are defined as in Group D. Y is at position 4 and is defined as in Group D.

A still further group of compounds, hereafter referred to as Group F, are compounds wherein $R_1$, $R_2$, X and Y are as defined in Group E and the location of the

groups are at the 2 and 6 positions.

A further group of compounds, hereafter referred to as Group G, are compounds wherein the location of the

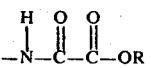

groups, X and Y are defined as in Group F, with the proviso that halogen is fluoro, chloro, and bromo. $R_1$ and $R_2$ are the same or different and are selected from the group consisting of alkyl of seven to ten carbon atoms, inclusive, and

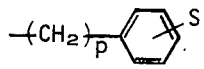

wherein $p$ is 1 or 2 and S is selected from the group consisting of hydrogen, alkyl of 1 to 4 carbon atoms, inclusive, alkoxy of 1 to 4 carbon atoms, inclusive, fluoro, chloro, bromo, cyano, and carboxy.

A still further group of compounds are compounds of successive Groups D, E, F and G with the proviso that the N-oxide is excluded and $R_1$ and $R_2$ are defined as in Group G.

Preferred $R_1$ and $R_2$ groups are the above scopings when $R_1$ is the same as $R_2$. It should be noted that when $R_1$ and $R_2$ are the same, neither $R_1$ nor $R_2$ can be hydrogen or a physiologically acceptable metal or amine cation.

Most preferred groups are the dibenzyl and diphenylethyl dioxamates.

As employed in the above disclosure and throughout the specification, the term "halogen" includes fluoro, chloro, bromo, and iodo. The phrase "alkyl of 1 to 6 carbon atoms, inclusive," includes methyl, ethyl, propyl, butyl, pentyl, hexyl and isomers thereof. Illustrative examples of isomers are isopropyl, tert. butyl, neopentyl, and 2,3-dimethylbutyl. When alkyl is limited to a lesser number of carbon atoms, the same scoping is intended within that number of carbon atoms. The phrase "alkyl of 2 to 12 carbon atoms, inclusive" includes heptyl, octyl, nonyl, decyl, undecyl, dodecyl and isomers thereof. Illustrative examples of isomers are isoheptyl, 2,2,4-trimethyloctyl, 2-propyl-4-methylpentyl, isodecyl, tert. undecyl and isododecyl.

The phrase "a physiologically acceptable metal or amine cation" is that metal or amine which is accepted in an essentially non-toxic manner by a mammal. Illustrative examples of such metals are the alkali metals, e.g., lithium, sodium and potassium, and the alkaline earth metal, e.g., magnesium and calcium. Other metals, e.g., aluminum, zinc and iron are also within the scope of this invention. Illustrative of the amines are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about eighteen carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, glactamine, N-methylglucamine, N-methylglucosamine, ephedrine, phenylephrine, procaine, and the like. Also included within the amine scope are quaternary amines such as ammonium, tetramethylammonium, tetraethylammonium, benzyltrimethylammonium, phenyltriethylammonium, and the like.

Physiologically acceptable acid addition salts refer to the salts which can be prepared at the nitrogen of the pyridine ring. Illustrative of these salts are hydrochloric, hydrobromic, hydriodic, nitric, sulfuric, oxalic, cyclohexanesulfamic, salicyclic, and the like.

The compounds of the invention can be prepared by methods known in the art. For example, methods outlined in U.S. Pat. No. 3,639,249, Column 3, line 38, to Column 5, line 18, can be used with facility. The appropriately substituted diaminopyridines are suitable starting materials. These compounds are reacted with an $R_1$ substituted oxalyl halide, $R_1$ not being a physiologically acceptable metal or amine cation in a suitable solvent and base to form a dioxamate of FIG. 1. The ester can then be transesterified with known reagents and conditions to form a different ester. If less than stoichiometric quantities are employed in the transesterification, esters where $R_1$ and $R_2$ differ are readily prepared. After formation of the ester, less than stiochiometric quantities of reagents can be employed to prepare the half metal, half acid, or half amine salt — the other half of the molecule being the ester moiety.

As stated previously, the appropriate substituted diamino pyridine is reacted with an $R_1$ oxalyl halide, for example, butyloxalylchloride to form the dioxamate. The reaction is carried out in base and solvent at the standard conditions, as exemplified by the art. Examples of suitable solvents are dimethylformamide, dioxane, and tetrahydrofuran. Appropriate bases include triethylamine, N-methylmorpholine, dimethylpiperazine and N-methylpiperidine.

Alternatively, A $diR_1$ oxalate is employed. The appropriately substituted diamino pyridine is heated together with the oxalate or an additional solvent such as a xylene or diphenyl ether if desired, thereby forming the dioxamate. The temperature is from about 25°C. to the reflux temperature of the system, preferably temperature between about 100°C. and the reflux temperature.

The N-oxide derivative of the pyridyl dioxamate can be readily prepared by oxidation of the diester with an oxidizing agent, such as m-chloroperoxy benzoic acid.

The appropriately X and Y substituted diaminopyridine starting materials are prepared by conventional substitution means well known in the art. These means depend somewhat upon the substituent itself, the placement of the substituent and the placement of the oxamic group.

The particular

substituents can be prepared by converting the corresponding diamino or dinitro pyridinecarboxylic acid, for example, to the ester, amide, etc., by standard methods. This can be done prior to the preparation of the dioxamate from the substituted diamino starting material.

An additional route of preparing the starting materials, (II), for example, is by reacting a substituted dihalopyridine, for example, dichloropyridine (V) with ammonia under pressure and elevated temperature to produce the substituted diaminopyridine starting material (II)

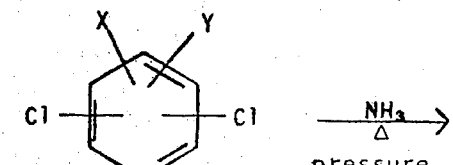

(V)

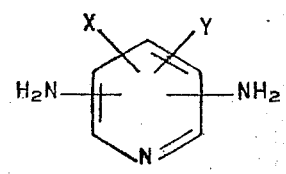

(II)

Illustrative examples of starting materials of FIG. 11 are below.

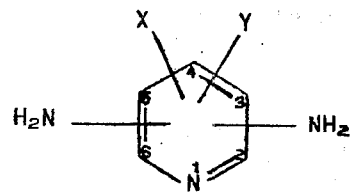

(II)

TABLE 1

| 2,6-diamino | | 2,4-diamino | | 2,5-diamino | | 3,5-diamino | |
|---|---|---|---|---|---|---|---|
| X | Y | X | Y | X | Y | X | Y |
| 4-BuO | H | 3-NO₂ | H | 3-CO₂H | H | 2-OBu | H |
| 4-EtO | H | 5-NO₂ | H | 3-Cl | H | 2-Cl | H |
| 4-MeO | H | 3-NO₂ | 6-C₃H₇ | 3-C₆H₅ | H | 2-OEt | H |
| 3-NO₂ | H | 6-Br | H | 3-CN | H | 2-OMe | H |
| 3-NO | H | 6-Br | 3-CN | 3-CF₃ | H | 2-O-Pr | H |
| 4-Cl | H | 6-Cl | 3-CN | 3-CH₃ | H | 4-C₆H₅ | H |
| 3-I | 5-I | 6-F | 3-CN | 3-nBu | H | 4-CN | H |
|  |  | 6-Et | 3-CN | 3-Et | H | 4-CF₃ | H |
| 4-Et | H | 6-C₆H₅ | H | 3-Pr | H | 4-CH₃ | H |
| 4-i-pentyl-oxy | H | 6-CN | H | 3-NO₂ | H | 4-nBu | H |
| 4-CO₂H | H | 6-CF₃ | H | 4-CN | H | 4-Et | H |
| 3-CO₂H | 5-CO₂H | 6-CH₃ | H | 4-CF₃ | H | 4-Pr | H |
| 4-i-OC₃H₇ | H | 6-nBu | H | 4-NO₂ | H | 4-NO₂ | H |
|  |  | 6-Et | H | 6-CN | H | 4-CN | 2-Cl |
| 4-n-pentyl-oxy | H | 6-Pr | H | 6-CF₃ | H | 4-Et | 2-Cl |

TABLE 1-continued

| 2,6-diamino | | 2,4-diamino | | 2,5-diamino | | 3,5-diamino | |
|---|---|---|---|---|---|---|---|
| X | Y | X | Y | X | Y | X | Y |
| 3-phenyl | H | 6-NO$_2$ | H | 6-NO$_2$ | H | 4-CF$_3$ | 2-Et |
| 3-Br | H | 6-CN | 3-Cl | 3-CN | 6-H | 4-Pr | 2-Br |
| 3-MeO | H | 6-CF$_3$ | 3-Et | 6-Cl | 3-CN | 4-NO$_2$ | 2-OMe |
| 4-Br | H | 6-Pr | 3-Br | 3-CF$_3$ | 6-Cl | 4-Cl | 2-Et |
| 3-OEt | 5-OEt | 6-NO$_2$ | 3-OMe | 3-Cl | 6-CF$_3$ | 4-Et | 2-CF$_3$ |
| 3-CN | 5-CN | 6-CH$_3$ | 5-Cl | 3-OMe | 6-Et | 4-Br | 2-Pr |
| 4-C$_6$H$_5$ | H | 6-OEt | 5-CF$_3$ | 3-COOH | 6-Br | 4-OMe | 2-NO$_2$ |
| 4-CN | H | 5-Cl | 3-CN | 3-iPr | 4-iPr | 2-OMe | 6-OMe |
| 4-CF$_3$ | H | 5-CN | 3-Cl | 3-CN | 4-CN | 2-CH$_3$ | 6-OEt |
| 4-CH$_3$ | H | 5-Cl | 3-COOH | 3-Et | 4-Cl | 2-Cl | 6-Cl |
| 4-nBu | H | 5-COOH | 3-Cl | 3-Cl | 4-Et | 2-CF$_3$ | 6-Cl |
| 4-Et | H | 5-Me | 3-CF$_3$ | 3-OEt | 4-COOH | 2-CN | 6-Cl |
| 4-iPr | H | 5-OEt | 3-NO$_2$ | | | 2-OPr | 6-COOH |
| 4-NO$_2$ | H | 5-Et | 3-iOPr | | | 2-COOH | 6-COOH |
| 4-CN | 3-Cl | | | | | | |
| 4-CF$_3$ | 3-Et | | | | | | |
| 4-Pr | 3-Br | | | | | | |
| 4-NO$_2$ | 3-OMe | | | | | | |
| 3-CH$_3$ | 5-Cl | | | | | | |
| 3-OEt | 5-CF$_3$ | | | | | | |
| 4-Cl | 3-CN | | | | | | |
| 4-CN | 3-Cl | | | | | | |
| 4-Cl | 3-COOH | | | | | | |
| 3-COOH | 4-Cl | | | | | | |
| 4-Me | 3-CF$_3$ | | | | | | |
| 4-OEt | 3-NO$_2$ | | | | | | |
| 4-Et | 3-iOPr | | | | | | |

TABLE II

Each of the starting materials of TABLE I are converted to a dioxamate of FIG. 1 where $R_1$ and $R_2$ are the same and are illustratively exemplified by the following:

$R_1 = R_2$

C$_7$H$_{15}$
i-C$_8$H$_{17}$
2,4-diethylpentyl
i-decyl
dodecyl
cyclobutyl
cyclopentyl
cyclohexyl
cycloheptyl
cyclooctyl
phenyl
benzyl
phenethyl
α,α-dimethylbenzyl
4-(phenyl)butyl
α,α-dimethylphenethyl
p-chlorophenyl
o-isopropylbenzyl
m-pentylphenethyl
3-(p-isohexylphenyl)propyl
m-methoxyphenethyl
p-butoxyphenyl
m-phenylbenzyl
3-(o-fluorophenyl)propyl
m-bromophenethyl
p-(trifluoromethyl)phenyl
m-hydroxyphenethyl
o-aminobenzyl
m-nitrophenyl
p-carboxyphenethyl
m-cyano-α,α-dimethylbenzyl
4-(o-cyanophenyl)butyl
o-(methylamino)phenyl
m-(diethylamino) benzyl
p-(dibutylamino)phenethyl
o-(ethylmethylamino)α,α-dimethylbenzyl
4-[m-(propylamino)phenyl]butyl
2-aminoethyl
3-(methylamino)propyl
4-(ethylamino)butyl
2-(methylpropylamino)ethyl
1-(butylethylamino)-1-methyl
2-(1-azetidinyl)ethyl
3-(1-pyrrolidinyl)propyl
4-(hexahydro-1H-azepin-1-yl)butyl
4-(o-isopropoxyphenyl)butyl

TABLE III

The compounds of Table II are converted to unsymmetrical esters ($R_1 \neq R_2$) by standard means.

TABLE IV

The compounds of Tables II and III are converted by standard means to half esters where either $R_1$ or $R_2$ is hydrogen or a physiologically acceptable metal or amine cation.

The following example is a compound in accordance with this invention. The compound is not intended to limit but merely to exemplify the invention.

EXAMPLE 1

Dibenzyl N,N'-(2,6-pyridinediyl)dioxamate 2,6-Diaminopyridine (10.9 g. 0.10 mole) is dissolved in 150 ml. of anhydrous dimethylformamide containing triethylamine (22.0 g. 0.22 mole). The stirred reaction mixture is cooled in an ice bath and benzyl oxalyl chloride (41.6 g. 0.21 mole) is added dropwise. The reaction mixture is stirred at room temperature for eighteen hours. The reaction mixture is poured into ice-water (1 l.). The resulting solid product is collected by filtration, washed with water, and dried at 60° in vacuo. Benzyl oxalyl chloride is prepared in the manner of Number 3234, of the same invention entity as of this case and filed on the same day. The Ser. No. is 477,816.

The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of FIG. I. The preferred method of administration is by inhalation into the lung by means of an aerosol liquid or powder for insufflation.

For oral administration, either solid or fluid unit dosage forms can be prepared. For preparing solid compositions such as tablets, the compound of FIG. I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hyroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung. For treatment of allergic conditions of the nose, such as rhinitis, compositions adapted for contact with nasal linings are preferred.

Compositions for inhalation are of three basic types: (1) a powder mixture preferably micropulverized with particle size, preferably from about 1 to about 5 microns; (2) an aqueous solution or suspension to be sprayed with a nebulizer; and (3) an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dispersing a compound of the FIG. I in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl, chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genetron 142-A") and monochlorotrifluoromethane (Freon 13).

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampuls, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 0.05 to about 20 mg. of compound in a single dose, administered parenterally or by inhalation in the compositions of this invention, are effective for preventing allergy attacks. More specifically, the single dose is from about 0.2 to about 20 mg. of compound. The oral and rectal dose is from about 1.0 to about 300 mg. in a single dose. More specifically, the single dose is from about 10 to about 150 mg. of compound. The dosage to be administered can be repeated up to four times daily.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune diseases, exercise induced asthma, stress induced asthma, systemic anaphylaxis, and bird fancier's disease.

EXAMPLE 2

A lot of 10,000 tablets, each containing 1 mg. of Dibenzyl N,N'-(2,6-pyridinediyl)dioxamate is prepared from the following types and amounts of ingredients:

| | |
|---|---|
| Dibenzyl N,N'-(2,6-pyridinediyl)-dioxamate | 10 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever or asthma attacks at a dose of one tablet every six hours.

EXAMPLE 3

One thousand tablets, each containing 4 mg. of Dibenayl N,N'-(2,6-pyridinediyl)dioxamate are prepared from the following types and amounts of ingredients:

| | |
|---|---|
| Dibenzyl N,N'-(2,6-pyridinediyl)-dioxamate | 4 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 4

A sterile preparation suitable for intramuscular injection and containing 0.1 mg. of Dibenzyl N,N'-(2,6-pyridinediyl)dioxamate in each milliliter is prepared from the following ingredients:

| | | |
|---|---|---|
| Dibenzyl N,N'-(2,6-pyridinediyl)-dioxamate, micronized | 0.1 | Gm. |
| Benzyl benzoate | 200 | ml. |
| Methylparaben | 1.5 | Gm. |
| Propylparaben | 0.5 | Gm. |
| Cottonseed oil q.s. | 1,000 | ml. |

One milliliter of this sterile preparation is injected for prophylactic treatment of allergic rhinitis.

EXAMPLE 5

Six hundred ml. of an aqueous dispersion containing 3.0 mg. of the Dibenzyl N,N'-(2,6pyridinediyl)dioxamate per ml. is prepared as follows:

| | | |
|---|---|---|
| Dibenzyl N,N'-(2,6-pyridinediyl)-dioxamate, micronized | 1.8 | Gm. |
| Sodium chloride | 5 | Gm. |
| Water for injection q.s. | 600 | ml. |

The compound of the above formulation and sodium chloride are dispersed in sufficient water to make 600 ml. and sterilized.

The liquid is placed in nebulizers designed to deliver 0.25 ml. per spray.

The liquid is inhaled into the lungs every four to six hours for prevention of asthmatic attacks.

EXAMPLE 6

A powder mixture consisting of 0.2 gram of Dibenzyl N,N'-(2,6-pyridinediyl)dioxamate and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 7

A powder mixture consisting of 0.2 gram of diphenethyl N,N'-(2,6-pyridinediyl)dioxamate and sufficient lactose to make five grams of mixture is micropulverized and placed in an insufflator designed to delivery 50 mg. of powder per dose.

The powder is inhaled into the lungs every four to six hours for prevention of asthmatic attacks.

The powder is inhaled intranasally every four hours for prevention of rhinitis.

EXAMPLE 8

Twelve grams of an aerosol composition are prepared from the following ingredients:

Dibenzyl N,N'-(2,6-pyridinediyl)-

-continued

| | |
|---|---|
| dioxamate, micronized | 0.100 Gm. |
| Freon 12 | 1.440 Gm. |
| Freon 114 | 2.160 Gm. |
| Water | 7.700 Gm. |
| Sorbitan monoleate | 0.600 Gm. |

The compound is dispersed in the water and chilled to −30°C. and added to the chilled Freons. The twelve grams of compositions are added to a 13 ml. plastic coated bottle and capped with a metering valve. The metering valve releases 80 mg. of composition in an aerosol. The aerosol is inhaled every four to six hours for prevention of asthmatic attacks.

EXAMPLE 9

After allowing for the differing solubilities of the compounds and the activity of the particular compound as measured, for example, by the in vivo rat passive cutaneous anaphylaxis assay, a suitable quantity of each of the compounds of Table II through Table IV and Example 1 is substituted for the active compound in the compositions and uses of Examples 2 through 8. Results showing anti-allergy activity are obtained.

It should be noted that in all the compositions and treatment examples of this patent application, the quantity of drug employed refers to the acid equivalent.

The diesters of this patent application, preferably the dibenzyl and diphenethyl compounds, can have longer durations of activity.

When repeated administration is desired, the compounds of this application which have a relatively short duration of activity can be administered in a priming dose-maintenance dose regimen as described in U.S. Ser. No. 403,677 at Page 21, line 28, to Page 22, line 16.

We claim:
1. Compound of the formula

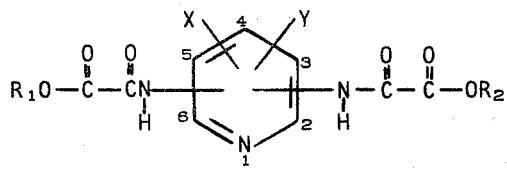

and N-oxides thereof wherein each

group is located anywhere on the carbon ring with the proviso that one group cannot be ortho to the other group;

X and Y are the same or different and are selected from the group consisting of hydrogen, alkyl of 1 to 4 carbon atoms, inclusive, phenyl, alkoxy from 1 to 4 carbon atoms, inclusive, nitro, amino, trifluoromethyl, halogen, and

wherein D is selected from the group consisting of hydrogen, alkyl of 1 to 6 carbon atoms, inclusive, and a physiologically acceptable metal or amine cation;

$R_1$ and $R_2$ are the same or different and are selected from the group consisting of hydrogen; a physiologically acceptable metal or amine cation; alkyl of 7 to 12 carbon atoms, inclusive; cycloalkyl of 4 to 8 carbon atoms, inclusive;

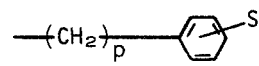

wherein $p$ is an integer of 0 to 4, inclusive, and S is selected from the group consisting of hydrogen, alkyl of 1 to 6 carbon atoms, inclusive, phenyl, halogen, trifluoromethyl, hydroxy, alkoxy of 1 to 4 carbon atoms, inclusive, amino, nitro, carboxy, and

wherein $R_3$ and $R_4$ are the same or different and are selected from the group consisting of hydrogen and alkyl of one to four carbon atoms, inclusive; with the proviso that when $p$ is zero, S is not hydrogen; and

wherein $b$ is an integer of 2 to 4, inclusive, and $R_5$ and $R_6$ are the same or different and are selected from the group consisting of hydrogen and alkyl of one to four carbon atoms, inclusive, with the further proviso that when one of $R_1$ and $R_2$ is hydrogen or a physiologically acceptable metal or amine cation, the other variable is not hydrogen or a metal or amine cation; and physiologically acceptable acid addition salts thereof.

2. Compound in accordance with claim 1 wherein X and Y are the same or different and are selected from the group consisting of hydrogen, alkyl of 1 to 4 carbon atoms, inclusive, phenyl, alkoxy of 1 to 4 carbon atoms, inclusive, nitro, trifluoromethyl, and

3. Compound in accordance with claim 2 wherein the

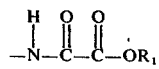

group is at the 2 or 5 position and when at the 2 position,

is at the 6 position and when the $$\underset{\mathrm{H\ O\ O}}{-\mathrm{N-C-C-OR_1}}$$

group is at the 3 position, $$\underset{\mathrm{H\ O\ O}}{-\mathrm{N-C-C-OR_2}}$$

is at the 5 position.

4. Compound in accordance with claim 3 wherein X is hydrogen, Y is selected from the group consisting of hydrogen, alkyl of one to four carbon atoms, inclusive, alkoxy of one to four carbon atoms, inclusive, nitro trifluoromethyl, halogen, and $$\underset{\mathrm{O}}{\mathrm{C-OD}};$$

$R_1$ and $R_2$ are the same or different and are selected from the group consisting of alkyl of 7 to 10 carbon atoms, inclusive, and $$-(CH_2)_p-\underset{}{\bigcirc}-S$$

wherein $p$ is an integer of 0 to 4, inclusive, and S is selected from the group consisting of hydrogen, alkyl of 1 to 4 carbon atoms, inclusive, alkoxy of 1 to 4 carbon atoms, inclusive, halogen and carboxy, with the proviso that when $p$ is zero, S is not hydrogen.

5. Compound in accordance with claim 4 wherein Y is at postion 4.

6. Compound in accordance with claim 5 wherein $$\underset{\mathrm{H\ O\ O}}{-\mathrm{N-C-C-OR_1}}$$

is at position 2 and $$\underset{\mathrm{H\ O\ O}}{-\mathrm{N-C-C-OR_2}}$$

is at position 6.

7. Compound in accordance with claim 6 wherein when Y is halogen, halogen is selected from the group consisting of fluoro, chloro and bromo;

$R_1$ and $R_2$ are the same or different and are selected from the group consisting of alkyl of 7 to 10 carbon atoms, inclusive, and $$-(CH_2)_p-\underset{}{\bigcirc}-S$$

wherein $p$ is 1 or 2 and S is selected from the group consisting of hydrogen, alkyl of 1 to 4 carbon atoms, inclusive, fluoro, chloro, bromo, and carboxy.

8. Compound in accordance with claim 4 with the proviso that N-oxides are excluded and $R_1$ and $R_2$ are selected from the group consisting of alkyl of 7 to 10 carbon atoms, inclusive, and $$-(CH_2)_p-\underset{}{\bigcirc}-S$$

wherein $p$ is 1 or 2 and S is selected from the group consisting of hydrogen, alkyl of 1 to 4 carbon atoms, inclusive, fluoro, chloro, bromo, and carboxy.

9. Compound in accordance with claim 5 with the proviso that N-oxides are excluded and $R_1$ and $R_2$ are selected from the group consisting of alkyl of 7 to 10 carbon atoms, inclusive, and $$-(CH_2)_p-\underset{}{\bigcirc}-S$$

wherein $p$ is 1 or 2 and S is selected from the group consisting of hydrogen, alkyl of 1 to 4 carbon atoms, inclusive, fluoro, chloro, bromo, and carboxy.

10. Compound in accordance with claim 6 with the proviso that N-oxides are excluded and $R_1$ and $R_2$ are selected from the group consisting of alkyl of 7 to 10 carbon atoms, inclusive, and $$-(CH_2)_p-\underset{}{\bigcirc}-S$$

wherein $p$ is 1 or 2 and S is selected from the group consisting of hydrogen, alkyl of 1 to 4 carbon atoms, inclusive, fluoro, chloro, bromo, and carboxy.

11. Compound in accordance with claim 7 with the proviso that N-oxides are excluded.

12. Compound in accordance with claim 1 wherein $R_1$ is the same as $R_2$.

13. Compound in accordance with claim 4 wherein $R_1$ is the same as $R_2$.

14. Compound in accordance with claim 7 wherein $R_1$ is the same as $R_2$.

15. Dibenzyl N,N'(2,6-pyridinediyl)dioxamate.

* * * * *

UNITED STATES PATENT AND TRADEMARK OFFICE
CERTIFICATE OF CORRECTION

PATENT NO. : 3,980,660
DATED : September 14, 1976
INVENTOR(S) : John B. Wright, Charles M. Hall, and Anthony A. Sinkula It is certified that error appears in the above—identified patent and that said Letters Patent is hereby corrected as shown below:

Column 2, line 2; change "trigluoromethyl" to --trifluoromethyl--.

Column 4, line 17; change "2" to --seven--.

Column 4, line 27; change "metal," to --metals,--.

Column 6, Table 1, under X of 2,4-diamino; change "6-Et" to --6-1--.

Column 8, line 34; change "-methyl" to -- -methylethyl--.

Column 11, lines 58-59; change "Dibenayl" to --Dibenzyl--.

Column 12, line 25; change "(2,6pyridinediyl)" to --(2,6-pyridinediyl)--.

Column 12, lines 56-57; change "delivery" to --deliver--.

Column 15, line 17; change "nitro" to --nitro,--.

Signed and Sealed this

First Day of July 1980

[SEAL]

Attest:

SIDNEY A. DIAMOND

Attesting Officer

Commissioner of Patents and Trademarks